United States Patent
Harrison et al.

(10) Patent No.: US 7,039,466 B1
(45) Date of Patent: May 2, 2006

(54) SPATIAL DECIMATION STIMULATION IN AN IMPLANTABLE NEURAL STIMULATOR, SUCH AS A COCHLEAR IMPLANT

(75) Inventors: William Vanbrooks Harrison, Valencia, CA (US); Michael A. Faltys, Northridge, CA (US)

(73) Assignee: Advanced Bionics Corporation, Valencia, CA (US)

( * ) Notice: Subject to any disclaimer, the term of this patent is extended or adjusted under 35 U.S.C. 154(b) by 148 days.

(21) Appl. No.: 10/833,427

(22) Filed: Apr. 28, 2004

Related U.S. Application Data (60) Provisional application No. 60/466,595, filed on Apr. 29, 2003.

(51) Int. Cl.
 *A61N 1/36* (2006.01)
(52) U.S. Cl. .............................. 607/56; 607/55; 607/57
(58) Field of Classification Search .................... 607/2, 607/45, 55–57
 See application file for complete search history.

(56) References Cited

U.S. PATENT DOCUMENTS

| | | | |
|---|---|---|---|
| 3,751,605 A | 8/1973 | Michelson | |
| 4,400,590 A | 8/1983 | Michelson | |
| 4,495,384 A | 1/1985 | Scott et al. | |
| 4,819,647 A | 4/1989 | Byers et al. | |
| 5,603,726 A | 2/1997 | Schulman et al. | |
| 5,626,629 A | 5/1997 | Faltys et al. | |
| 5,938,691 A | 8/1999 | Schulman et al. | |
| 6,067,474 A | 5/2000 | Schulman et al. | |
| 6,078,838 A | 6/2000 | Rubinstein | |
| 6,129,753 A | 10/2000 | Kuzma | |
| 6,157,861 A | 12/2000 | Faltys et al. | |
| 6,195,585 B1 | 2/2001 | Karunasiri et al. | |
| 6,205,360 B1 | 3/2001 | Carter et al. | |
| 6,208,882 B1 | 3/2001 | Lenarz et al. | |
| 6,219,580 B1 | 4/2001 | Faltys et al. | |
| 6,249,704 B1 | 6/2001 | Maltan et al. | |
| 6,289,247 B1 | 9/2001 | Faltys et al. | |
| 6,295,467 B1 | 9/2001 | Kollmeier et al. | |
| 6,415,185 B1 | 7/2002 | Maltan | |

FOREIGN PATENT DOCUMENTS

WO WO-03/015863 A2 2/2003

OTHER PUBLICATIONS

Rubinstein et al., "The Neurophysiological Effects of Simulated Auditory Prosthesis Simulation" Second Quarterly Progress Report NO1-DC-6-2111.

van Wieringen, et al., "Comparison of Procedures to Determine Electrical Stimulation Thresholds in Cochlear Implant Users", Ear and Hearing, vol. 22(6), (2001), pp. 528-538.

(Continued)

*Primary Examiner*—Robert E. Pezzuto
*Assistant Examiner*—Brian T. Gedeon
(74) *Attorney, Agent, or Firm*—Bryant R. Gold (57) ABSTRACT

A cochlear implant system, or other neural stimulation system, has the capability to stimulate fast enough to induce stochastic neural firing so as to restore "spontaneous" neural activity. The stimulation rate applied to the more distally-located electrodes of an electrode array connected to the implant system is reduced from the stimulation rate applied to the more proximally-located electrodes. Thus, in the case of a cochlear implant system, the apically-located regions within the cochlea are stimulated at a reduced rate in order to conserve power. Pulse widths of the reduced-rate pulses may further be increased, and amplitudes reduced, to further conserve power. As needed, a low-level random conditioner stimulation signal may be applied to the apical regions of the cochlea in order to ensure the occurrence of random neural firings.

14 Claims, 4 Drawing Sheets

OTHER PUBLICATIONS

Zeng, et al., "Loudness of Simple and Complex Stimuli in Electric Hearing", Annals of Otology, Rhinology & Laryngology, vol. 104 (9), (1995) pp. 235-238.

Zhang, et al., "Loudness of Dynamic Stimuli in Acoustic and Electric Hearing", J Acoust Soc Am, vol. 102(5) Pt. 1, (Nov. 1997), pp. 2925-2934.

Overstreet and Faltys inventors for AB-254U; U.S. Appl. No. 10/218,645, filed Aug. 13, 2002; entitled "Cochlear Implant and Simplified Method for Fitting Same".

Faltys inventor for AB-257U; U.S. Appl. No. 10/218,616, filed Aug. 13, 2002; entitled "Bionic Ear Programming System".

Segel, Overstreet, Kruger, and Mishra inventors for AB-313U; U.S. Appl. No. 10/651,653, filed Aug. 29, 2003; entitled "System and Method for Fitting a Cochlear Implant Sound Processor Using Alternative Signals".

Overstreet inventor for AB-362U; U.S. Appl. No. 10/647,372, filed Aug. 25, 2003; entitled "Enhanced Methods for Determining Iso-Loudness Contours for Fitting Cochlear Implant Sound Processors".

Maltan, Miller, and Harrison inventors for AB-376U; U.S. Appl. No. 10/662,615, filed Sep. 30, 2003; entitled "Cochlear Implant Sound Processor with Permanently Integrated Replenishable Power Source".

Overstreet, Litvak, and Faltys inventors for AB-378U; U.S. Appl. No. 10/698,097; filed Oct. 31, 2003; entitled "Multi-Electrode Stimulation to Elicit Electrically-Evoked Compound Action Potential."

Overstreet inventor for AB-379U; U.S. Appl. No. 10/698,098, filed Oct. 31, 2003; entitled "Method and System for Generating a Cochlear Implant Program Using Multi-Electrode Stimulation to Elicit the Electrically-Evoked Compound Action Potential".

SPATIAL DECIMATION STIMULATION IN AN IMPLANTABLE NEURAL STIMULATOR, SUCH AS A COCHLEAR IMPLANT

The present application claims the benefit of U.S. Provisional Patent Application Ser. No. 60/466,595, filed 29 Apr. 2003, which application is incorporated herein by reference.

BACKGROUND OF THE INVENTION

The present invention relates to implantable neural stimulators, such as a cochlear implant, and more particularly to an implantable neural stimulator wherein the bandwidth necessary for forward telemetry is reduced through the use of spatial decimation.

While the present invention relates to implantable neural stimulators, it will be described by way of example with reference to a cochlear implant, which represents one type of implantable neural stimulator. The principles of the present invention may be readily applied by those of skill in the art to all types of implantable neural stimulators. Hence, the invention is not limited to a cochlear implant.

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted by a cable connection through the patient's skin to an implanted multi-channel intracochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

Other improved features of a cochlear implant system are taught, e.g., in U.S. Pat. Nos. 5,626,629; 6,067,474; 6,157,861; 6,219,580; 6,249,704; and 6,289,247, each of which patents is incorporated herein by reference. Further enhancements are disclosed, e.g., in pending and co-owned U.S. patent application Ser. No. 10/218,645, filed Aug. 13, 2002, and U.S. patent application Ser. No. 10/218,616, filed Aug. 13, 2002, each of which patent applications is also incorporated herein by reference.

The implantable cochlear stimulators described in the '629, '474, '861 and '580 patents are also able to selectively control the pulse width of stimulating pulses that are applied through the electrode array to the cochlea, and the frequency at which the stimulating pulses are applied.

The new generation of cochlear implants that have the enhanced processing power, and which can provide multiple platforms for delivering electrical stimuli to the auditory nerve, including high frequency pulsitile stimulation having current pulses of controlled amplitude, width and frequency, are frequently referred to as a "bionic ear" implant.

The bionic ear, or equivalent, cochlear implants offer operating modes that provide very high-speed stimulation designed to increase temporal fine structure while also activating the stochastic resonance mode. The stochastic resonance mode has heretofore typically been lost to patients whose hearing loss qualifies them to receive a cochlear implant. The high rate stimulation mode advantageously has been found to provide performance benefits in, e.g., CNC word testing under quiet conditions, and also provides significant improvements in word testing in noisy conditions. Additionally, it has been estimated that the high rate stimulation mode will increase hearing fidelity to the point where significant improvements are achieved relative to the sound of music and other broadband acoustic signals. Thus, it is seen that the high rate stimulation mode represents a highly sought-after mode for inclusion in a cochlear implant. Similar stochastic resonance and other benefits are achievable with any neural implant device that utilizes high rate electrical stimulation parameters. See, e.g., PCT Publication No. WO 03/015863 A2, published 27 Feb. 2003, based on PCT International Patent Application Serial No. PCT/US02/25861, filed 13 Aug. 2002, incorporated herein by reference.

One problem resulting from the use of very fast stimulation rates with narrow biphasic pulses is that the system power requirements increase significantly. While the potential improvements in sound quality (or other neural performance) can be significant, these high rate modes can cause serious reduction in battery operating times. Hence, it is seen that there is a need for an operating mode that provides the benefits of high-speed stimulation, but which could be operated at significantly lower power levels.

SUMMARY OF THE INVENTION

The present invention addresses the above and other needs by providing a cochlear (or other neural) implant that provides the benefits of high rate stimulation at a lower power level through the use of spatial decimation.

One object of the high-speed stimulation mode, available in a bionic ear implant system, is to desynchronize the auditory nerve. See, e.g, U.S. patent application Ser. No. 10/218,645, filed Aug. 13, 2002, assigned to the same assignee as is the present application, and incorporated herein by reference, as well as PCT Publication No. WO 03/015863 A2, previously referenced. Such desynchronization produces random states of neural polarization and depolarization, thereby providing a reduction in thresholds and an increase in electrical dynamic range. In the presence of low frequency stimulation, below the refraction crossover stimulation rate of the neurons, most people with normal hearing achieve a synchronized neural response even though, in the absence of this stimulation, random fluctuations in neural firing might occur. Thus, if synchronous neural firings occur in the low frequency range in the presence of stimulation, then the application of high-rate pulses in this region produces little benefit and consumes excess power. Hence, in accordance with the teachings of the present invention, spatial decimation is used to reduce the frequency at which narrow-width, high-amplitude, fast-rate pulses are provided to the apical regions of the cochlea, thereby saving power. Because the cochlea is tonotopoically arranged, low frequencies are represented or sensed by providing stimuli in the apical region of the cochlea, and high frequencies are represented or sensed by providing stimuli in the basal region of the cochlea. Thus, the present invention saves power by using spatial decimation to reduce the stimulation rate tonotopically as the applied stimuli approach the apex of the cochlea.

In accordance with one aspect of the invention, power is reduced in a cochlear implant system by reducing the stimulation rate tonotopically.

It accordance with another aspect of the invention, power is reduced in a cochlea implant system without noticeably degrading the important part of the stochastic resonance effect or the presentation of relevant temporal fine structure, which are important features offered by the fast-rate, narrow-width, high-amplitude pulses generated by a bionic-ear type of implant system.

It is a feature of the invention, in accordance with one embodiment thereof, to provide a low level random conditioner stimulation signal to the apex region of the cochlea in order to ensure that random neural firings do occur in the low frequency region when low frequency stimulation energy is below a predetermined threshold.

Advantages offered by the present invention include, but are not necessarily limited to, the following: (1) the rate of stimulation to be applied to low-frequency regions of the cochlea may be significantly reduced at low frequencies below the refraction crossover rate and potentially into the crossover region based on patient performance; (2) the pulse width of pulses to be applied to low-frequency regions of the cochlea may be increased, thereby further reducing the power needed to generate adequate loudness growth; and (3) the forward telemetry data used by the implant system may be reduced, thereby providing a reduction in the forward telemetry bandwidth.

For purposes of the present application, "high rate" is defined as a stimulation rate greater than about 1.5 KHz to 2.0 KHz (i.e., stimulation where the period, T, between successive biphasic stimulation pulses is less than about 667 to 500 microseconds ($\mu$S)). "Pulsitile" stimulation is considered to be any pulsed stimulation, e.g., biphasic stimulation, where the pulse width, PW, of each phase of the biphasic pulse is less than about 21 $\mu$S, e.g., 11 $\mu$S, although in some instances it may be longer, e.g., 32 $\mu$S or as long as 75 $\mu$S. These definitional terms are illustrated in the waveform diagram presented in FIG. 1, described below.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
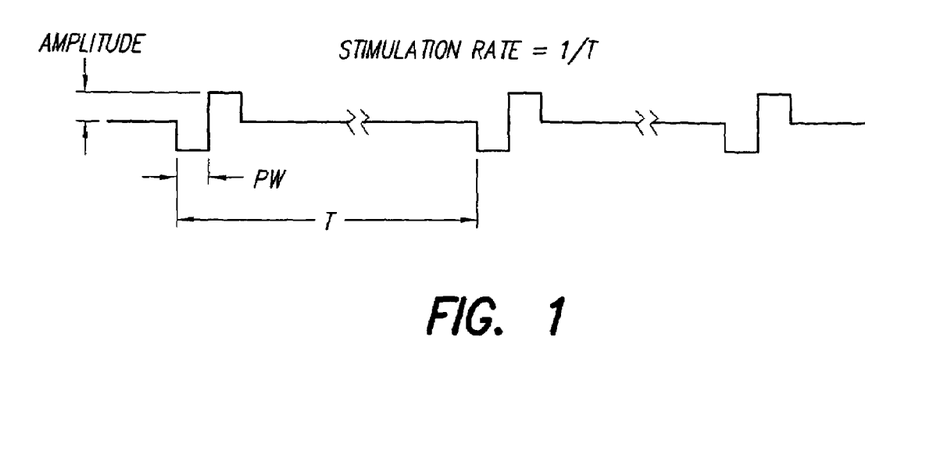
FIG. 1 is a current stimulation waveform that defines the stimulation rate (1/T) and biphasic pulse width (PW) associated with electrical stimuli, as those terms are used in the present application.

FIG. 1 shows a waveform diagram of a biphasic pulse train, and defines stimulation rate, pulse width and pulse amplitude as those terms are used in the present application.

Figure 2A:
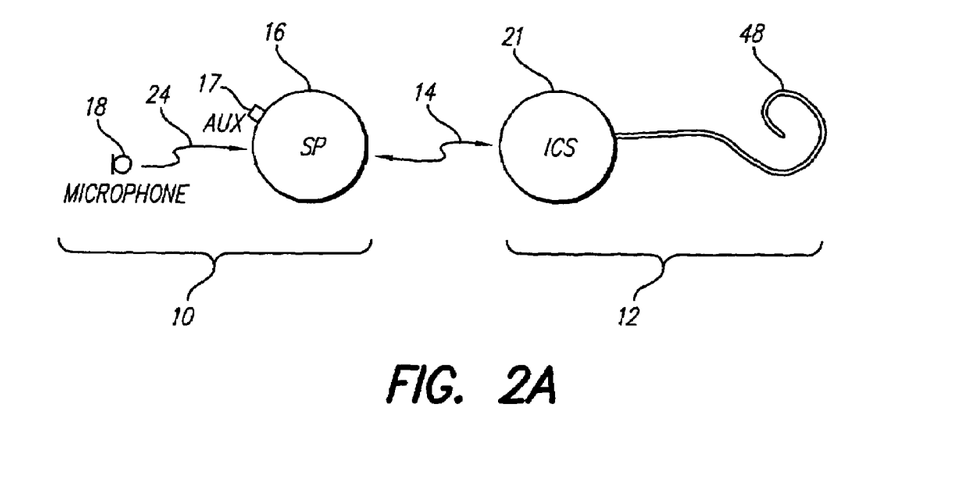
FIGS. 2A and 2B respectively show a cochlear implant system and a partial functional block diagram of the cochlear stimulation system, which system is capable of providing high rate pulsitile electrical stimuli in accordance with the invention.

FIG. 2A shows a bionic ear cochlear stimulation system that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. No. 4,819,647 or U.S. Pat. No. 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP16 to the ICS 21. In some embodiments, data and status signals may also be sent from the ICS 21 to the SP 16.

In a typical bionic ear implant system, as shown more particularly below in FIG. 2B, at least certain portions of the SP 16 are included within the implantable portion of the overall cochlear implant system, while other portions of the SP 16 remain in the external portion of the system. In general, at least the microphone 18 and associated analog front end (AFE) circuitry 22 will be part of the external portion of the system; and at least the ICS 21 and electrode array 48 are part of the implantable portion of the invention.

As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals, and may thus be considered as an acoustic transducer. The electrical signals are sent to the SP 16 over a suitable electrical or other link 24. The SP 16 processes these converted acoustic signals in accordance with a selected speech processing strategy in order to generate appropriate control signals for controlling the ICS 21. Such control signals specify or define the polarity, magnitude, location (which electrode pair receives the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy. Unlike early cochlear implant systems, the bionic ear implant system advantageously confines such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. In accordance with the present invention, spatial decimation is used to reduce the frequency at which stimulation pulses are applied through the more distally-located electrodes that stimulate the apical regions of the cochlea.

Current pulses applied in pulsitile stimulation patterns are generally biphasic pulses, as shown in FIG. 1, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type used with the present invention, it is common to apply a high rate biphasic stimulation pulse train to each of the pairs of electrodes of selected channels in accordance with a selected strategy, and modulate the pulse amplitude of the pulse train as a function of information contained within the sensed acoustic signal.

Figure 2B:
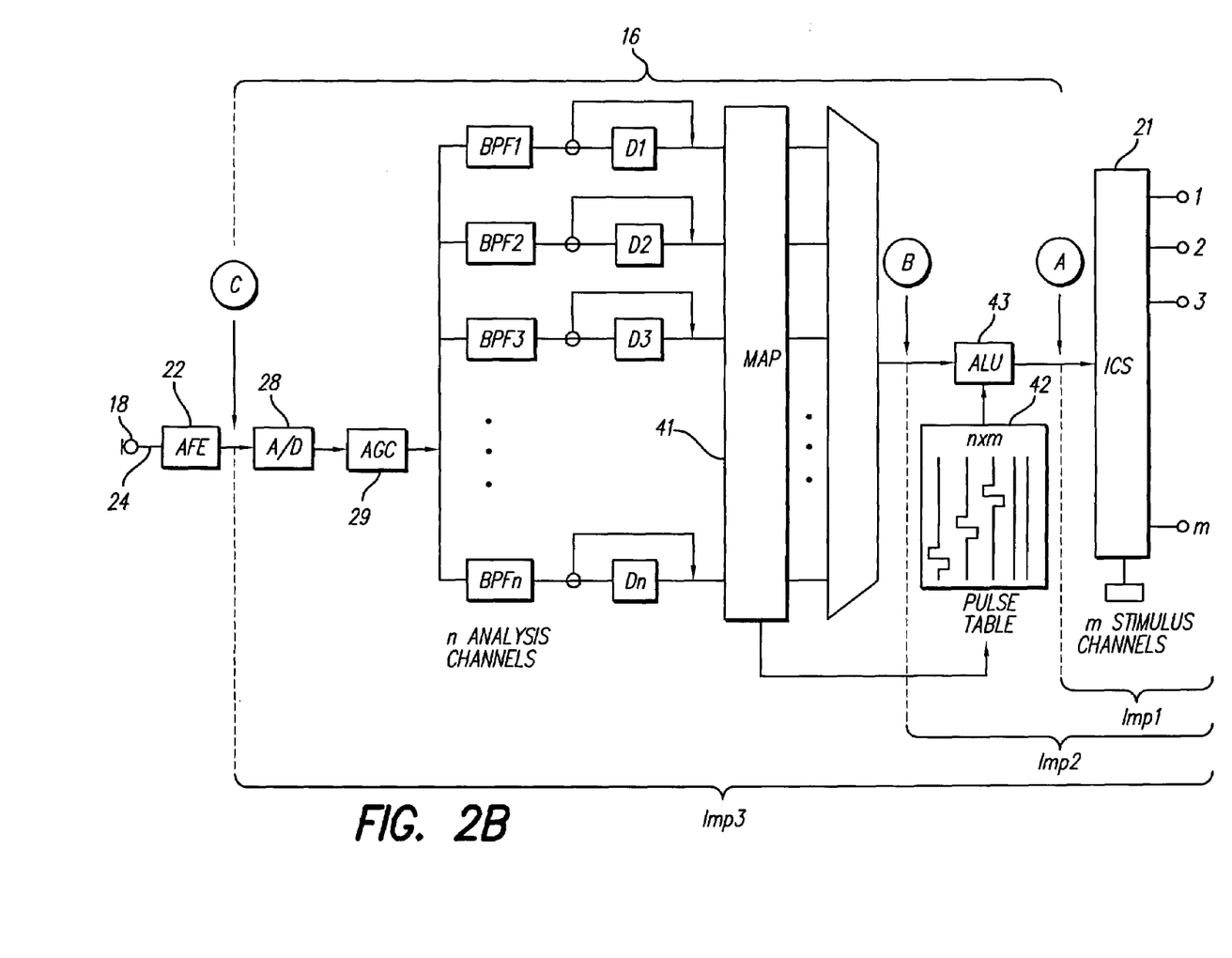

Turning next to FIG. 2B, a partial block diagram of a representative bionic ear cochlear implant is shown. More particularly, FIG. 2B shows a partial functional block diagram of the SP 16 and the ICS 21 of an exemplary bionic ear cochlear implant system capable of providing a high rate pulsitile stimulation pattern. That which is shown in FIG. 2B depicts the functions that are carried out by the SP 16 and the ICS 21. The actual electronic circuitry that is used to carry out these functions is not critical to understanding and practicing the present invention. It should also be pointed out that the particular functions shown in FIG. 2B are representative of just one type of signal processing strategy that may be employed (which divides the incoming signal into frequency bands, and independently processes each band). Other signal processing strategies could just as easily be used to process the incoming acoustical signal, and the present invention could still be used to provide spatial decimation stimulation.

A complete description of the functional block diagram of the bionic ear implant shown in FIG. 2B is found in U.S. Pat. No. 6,219,580, previously incorporated herein by reference. It is to be emphasized that the bionic ear functionality shown in FIG. 2B is only representative of one type of exemplary bionic ear implant, and is not intended to be limiting.

In the manner described in the U.S. Pat. No. 6,219,580 patent, the bionic ear implant functionally shown in FIG. 2B provides n analysis channels that may be mapped to one or more stimulus channels. That is, as seen in FIG. 2B, after the incoming sound signal is received through the microphone 18 and the analog front end circuitry (AFE) 22, it is digitized in an analog to digital (A/D) converter 28, and then subjected to appropriate gain control (which may include compression) in an automatic gain control (AGC) unit 29. After appropriate gain control, the signal is divided into n analysis channels, each of which includes a bandpass filter, BPFn, centered at a selected frequency. The signal present in each analysis channel is processed as described more fully in the U.S. Pat. No. 6,219,580 patent, and the signals from each analysis channel are then mapped, using mapping function 41, so that an appropriate stimulus current, of a desired amplitude and timing, may be applied through a selected stimulus channel to stimulate the auditory nerve.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 2B, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, a modern bionic ear implant, such as the CII Bionic Ear system manufactured by Advanced Bionics Corporation of Sylmar, Calif., advantageously puts at least a portion of the speech processor 16 within the implanted portion of the system. For example, a bionic ear implant may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

Future generations of bionic ear implant systems will incorporate more and more of the speech processor 16 within the implanted portion of the system. For example, a fully implanted speech processor 16 would incorporate all of the SP in the implanted portion, as indicated by the bracket labeled Imp3 in FIG. 2B. Such a fully implanted speech processor offers the advantage that the data input into the system, i.e., the data stream that passes through point (C), would need only have rate commensurate with the input acoustic signal.

The stimulation provided by a bionic ear implant, such as that shown in FIG. 2B, is premised on a stimulus pattern that induces stochastic, i.e., random, neural firing, which stochastic neural firing acts to restore "spontaneous" neural activity. Such stochastic neural firing results through application of a rapid stimulation pulse train applied by the speech processor circuits of the bionic ear cochlear implant. In operation, the high rate stimulus pattern provided by the invention stimulates individual neurons at a rate faster than the individual neurons can follow. This results in a randomization of inter-spike intervals, where the inter-spike interval is the time between successive neural firings for a given auditory neuron; or stated differently, inter-spike intervals represent the "firing patterns" of individual auditory nerve fibers. The inter-spike intervals, or firing patterns, of all auditory nerve fibers, even during the absence of sound, tend to be stochastic (random). Furthermore, these firing patterns are stochastic across the neural population. Advantageously, when the neuron is no longer phase-locked to the carrier pulse, its firing probability becomes a function of stimulus energy, and thus becomes more like "natural" hearing. Such randomization in a neural population better enables the population of neuron fibers to encode the fine details of sound. That is, the population of neuron fibers is able to encode what a single neuron fiber is not able to encode.

Figure 3:
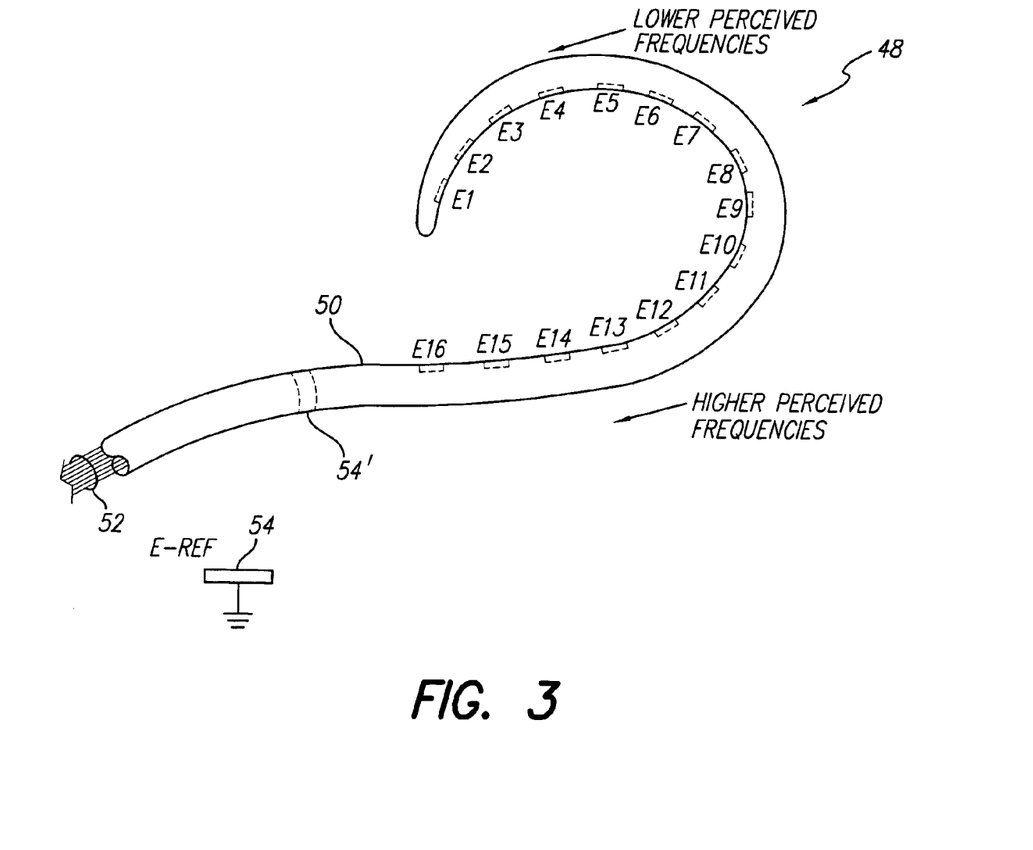
FIG. 3 shows a representative cochlear electrode array, including the spaced-apart electrode contacts thereon, and illustrates how the array curves in a spiral manner as it is inserted into the cochlea, and wherein when inserted into the cochlea the most distal electrode contacts stimulate neurons that trigger the perception of lower frequency sounds, and wherein the more proximal electrode contacts stimulate neurons that trigger the perception of higher frequency sounds.

Turning next to FIG. 3, an enlarged view of a representative cochlear implant electrode array 48 is illustrated. Such electrode array is adapted to be inserted into a human cochlea so that the auditory nerve may be electrically stimulated. The electrode array 48 has a multiplicity of spaced-apart electrode contacts, E1, E2, E3, .... Em, carried or embedded within the surface of, an elongate flexible carrier substrate 50. For the electrode array 48 shown in FIG. 3, there are sixteen such electrode contacts, i.e., m=16. Each electrode contact is connected to a respective wire that is included within a bundle 52 of wires (there may be, e.g., 18 wires included in the wire bundle 52) that are carried or embedded within the flexible carrier 50. Each wire is connected to appropriate electronic circuitry within the ICS 21 (FIG. 2A) so that a selected current stimulus having a prescribed amplitude, pulse width, and frequency, e.g., a current stimulus having a waveform as shown in FIG. 1, may be applied to body tissue in contact with, or near, the physical location of the electrode contact.

Typically, the current stimulus is applied using monopolar stimulation or bipolar stimulation. In monopolar stimulation, the current stimulus is applied between a selected electrode, e.g., one of the electrode contacts E1, E2, E3, ... E16, and a reference electrode 54 or 54'. It is common for the reference electrode 54 to be located on the case of the ICS 21, represented in FIG. 3 as the electrode E-REF. In such instance, the reference electrode E-REF is located some distance from the electrode contacts E1, E2, E3, ... E16. It is also possible for the reference electrode to be a band electrode 54' located proximally on the carrier 50. In bipolar stimulation, the current stimulus is applied between a selected pair of the electrode contacts E1, E2, E3, ... E16, e.g., between electrode contacts E3 and E4.

It is thus seen that, for the electrode array 48 shown in FIG. 3, there are sixteen potential stimulus channels through which an electrical stimulus may be applied to the inside of the cochlea. (Other electrode arrays, having fewer or more than sixteen electrode contacts could, of course, also be used.)

As is well known and documented in the art, the auditory nerve cells which are stimulated through application of an electrical stimulus applied through electrode contacts located inside the cochlea, are arranged tonotopically. That is, these nerve cells are arranged in an orderly tonotopic sequence, from high frequencies at the basal end of the cochlea spiral to progressively lower frequencies towards the apex of the cochlea. Such tonotopically arranged nerve cells may be considered as frequency-sensitive nerves. That is, they comprise a set or family of nerves that are physiologically arranged or located so that higher frequency stimulus signals are perceived differently than lower frequency stimulus signals.

When the electrode array 48 is inserted into the cochlea, stimuli applied to the more distally-located electrodes should be perceived as lower frequency tones than would stimuli applied to the more proximally-located electrodes. Stated differently, stimuli applied through, e.g., electrode contact E10 should be perceived as a higher frequency tone than would a stimuli applied through electrode contact E8.

As stated previously, an object of providing high-rate pulsitile stimulation using a cochlear implant like that shown in FIG. 2B is to desynchronize the auditory nerve. Such desynchronization produces random states of neural polarization and depolarization, thereby providing a reduction in thresholds and an increase in electrical dynamic range. In the presence of low frequency stimulation, below the refraction crossover stimulation rate of the neurons, most people with normal hearing achieve a synchronized neural response even though, in the absence of this stimulation, random fluctuations in neural firing might occur. Thus, because synchronous neural firings occur in the low frequency range in the presence of stimulation, it follows that the application of high-rate pulses in this region may produce little benefit at the cost of increased power consumption.

Hence, in accordance with the teachings of the present invention, spatial decimation is used to reduce the frequency at which high-rate pulsitile stimulation is provided to the apical regions of the cochlea, thereby saving power. Spatial decimation of the pulsitile stimulation applies the same concept used in discrete time signal processing systems where the sampling rate must be sufficient to satisfy the Nyquist sampling theorem. The Nyquist sampling theorem states that the sampling frequency must exceed twice the highest frequency in the signal being sampled. Spatial decimation is made possible because, as has been stated previously, the cochlea is a tonotopically arranged, with low frequencies being triggered when pulsitile stimuli are applied to the apical region of the cochlea and with high frequencies being triggered when pulsitile stimuli are applied to the basal region. Hence, in order to achieve its objective of reducing power without degrading performance, the present invention tonotopically reduces the rate at which pulsitile stimulation pulses are applied as the stimulation location approaches the apex of the cochlea.

Thus, it is seen that the present invention reduces the stimulation rate (the rate of the pulsitile stimulation applied through a given electrode) as a function of the electrode's position on the array. The more distally-located electrodes (those that will be in contact with neural tissue in the apical region of the cochlea when the electrode array is properly inserted into the cochlea) have the stimulation rate reduced the most. In other words, the stimulation rate is reduced tonotopically as the spatial stimulation site approaches the apex of the cochlea.

In one embodiment of the invention, a random low level conditioner stimulation signal may be used in order to ensure that random neural firings still occur when the low frequency stimulation energy is below a predetermined threshold.

Figure 4:
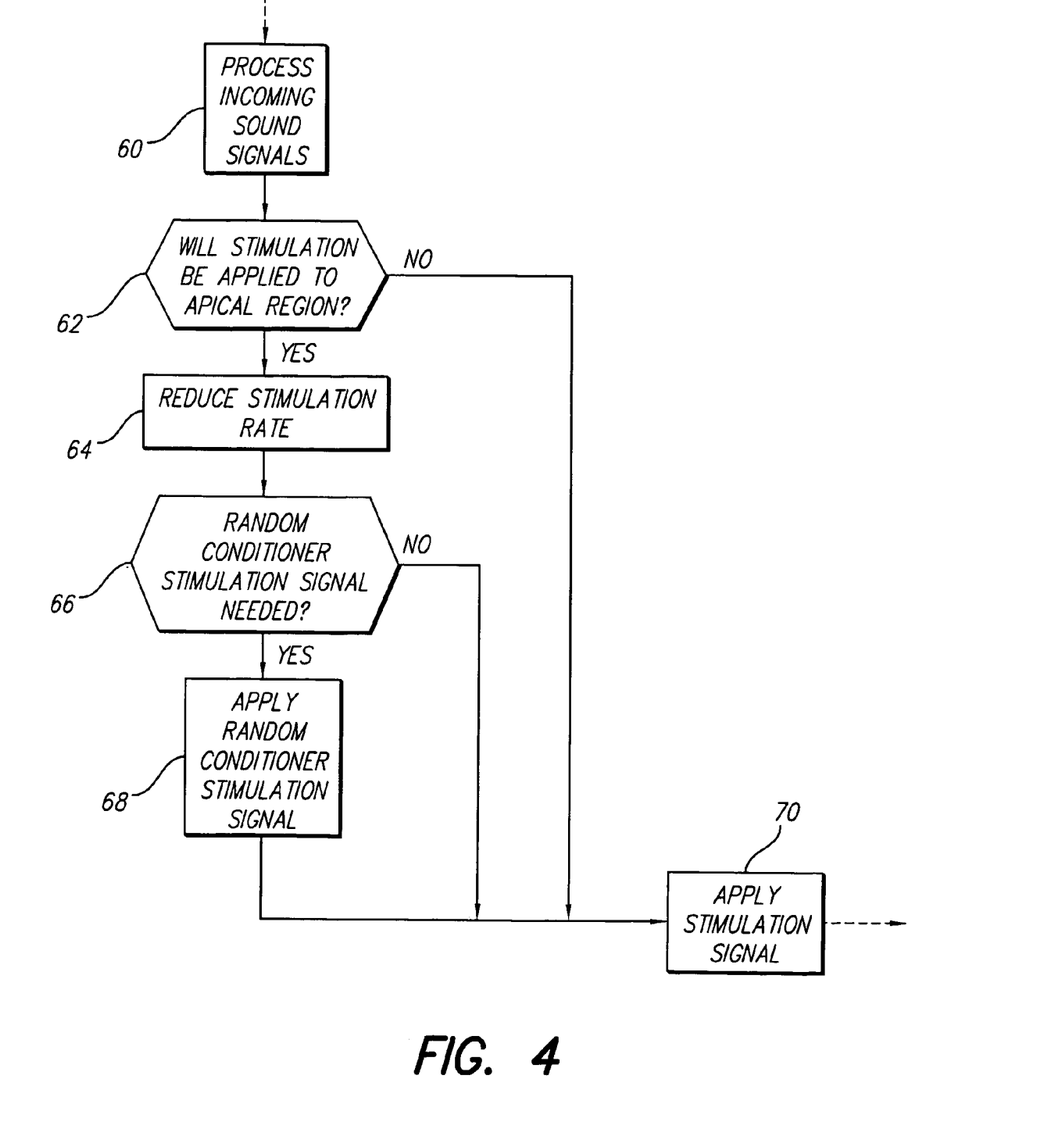
FIG. 4 shows a partial high level flow diagram that illustrates one exemplary method for carrying out the present invention.

In operation, one manner in which the invention may be implemented is shown in the flow diagram of FIG. 4. The method depicted in FIG. 4 may be embedded within the normal operating program of the cochlear (or other neural) implant system. In accordance with such operating program, incoming sound signals are processed (block 60) in accordance with the selected speech processing strategy of the implant system. During the course of such processing, stimulation signals are generated that are designated for application to specific electrodes of the electrode array. Once the stimulation signals are thus generated, or once the control signals that will create such stimulation signals are generated, a determination is made as to whether such stimulus signals are representative of low frequency sound (block 62). That is, a determination is made as to whether the stimulus signals are to be applied to the more distally-located electrodes of the electrode array. If so (YES branch of block 62), then the stimulation rate of the pulsitile signals is reduced (block 64) before the signals are applied to the designated electrode(s).

One way for reducing the stimulation rate is to allow only every pth pulse, where p is an integer, to be applied to the designated electrode. Thus, for example, if p is equal to 4, then only one pulse in every 4 pulses that would have otherwise (without the present invention) been applied to the designated electrode is applied to the designated electrode.

Additionally, the pulse width of the pulse that is applied may be increased, while its amplitude may be reduced, thereby reducing the power needed to generate adequate loudness growth.

In order to tonotopically reduce the stimulation rate, an appropriate algorithm may be used that reduces the stimulation rate as a function of the electrode contact through which the stimulus is to be applied. Such algorithm could take many forms. One form of an algorithm, assuming an electrode array with sixteen electrode contacts as shown in FIG. 3, would be as follows:

$$F_P(E_n) = 1 / [(M/2) + (1 - E_n)]$$

where
$F_P$ is the stimulation rate that is applied as a function of the electrode number, $E_n$, expressed as a fraction of the form $1/p$, where only 1 out of every p pulses is delivered to the electrode; and M is the number of electrodes.

Thus, if M=16 and the stimulus electrode is E1, or $E_n$=1 (i.e., the cathode is E1, the most distal electrode, see FIG. 3), then $$F_P = 1/[8 + (1-1)] = 1/8;$$

which means that only one out of every 8 pulses that would have been applied to electrode E1 is applied to electrode E1 when the present invention is enabled.

Similarly, assuming again that M=16, if the stimulus electrode is E6, then $$F_P = 1/[8 + (1 - 6)] = 1/3;$$

which means that only one out of every 3 pulses that would have been applied to electrode E6 is applied to electrode E6 when the invention is enabled.

It is to be emphasized, that the particular algorithm expressed above is only exemplary. Any suitable algorithm that reduces the stimulation rate tonotopically may be used.

In addition to an algorithm, the stimulation rate applied through a given electrode may be as defined in a table, such as Table 1 below. The values of p expressed in Table 1 may be programmable.

TABLE 1

| $E_N$ | p | $F_P$ |
|---|---|---|
| E1 | 5 | 1/5 |
| E2 | 5 | 1/5 |
| E3 | 4 | 1/4 |
| E4 | 4 | 1/4 |
| E5 | 3 | 1/3 |
| E6 | 3 | 1/3 |
| E7 | 2 | 1/2 |
| E8 | 2 | 1/2 |
| E9 | 1 | 1 |
| E10 | 1 | 1 |
| E11 | 1 | 1 |
| E12 | 1 | 1 |
| E13 | 1 | 1 |
| E14 | 1 | 1 |
| E15 | 1 | 1 |
| E16 | 1 | 1 |

Returning to FIG. 4, once the stimulation rate has been reduced (block 64), then a decision is made as to whether a random conditioner stimulation signal should be generated and applied to one or more distally-located electrodes (block 66). If so (YES branch of block 66), then a random conditioner signal having a low level, e.g., at or below a perception threshold, is applied to the appropriate electrodes (block 68).

The stimulation signal, e.g., a pulsitile stimulation sequence, is applied to the designated electrode contact(s), E1, E2, E3, . . . . En (block 70) whenever: (1) the electrodes through which the stimulation signal is applied are not in the apical region of the cochlea (NO branch of block 62); (2) a random conditioner stimulation signal is not needed (NO branch of block 66); or (3) after a random conditioner stimulation signal has been applied. The number of pulses in the pulsitile stimulation sequence that would be applied through the designated electrode(s) may be reduced, or the stimulation rate may be otherwise reduced, as a function of the tonotopic position in order to reduce the stimulation rate, as explained above, thereby conserving power.

Further, where the rate has been significantly reduced, the pulse widths of the pulses that remain may be increased, and their amplitudes decreased, so as to also reduce power consumption.

Moreover, where a fewer number of stimulation pulses are applied to the more apically-located electrodes, the amount of data that must be sent in the forward telemetry data channel is reduced. In turn, this allows for corresponding bandwidth reductions, which also further reduces power consumption.

As described above, it is seen that the present invention provides a cochlear implant system that offers the advantages of fast stimulation rates using narrow biphasic pulses while minimizing power consumption.

While the invention herein disclosed has been described by means of specific embodiments and applications thereof, numerous modifications and variations could be made thereto by those skilled in the art without departing from the scope of the invention set forth in the claims.

What is claimed is:

1. A cochlear implant system comprising:
    an electrode array having a multiplicity of spaced-apart electrode contacts at or near a distal end;
    an implantable pulse generator electrically connected to the electrode contacts of the electrode array;
    processing means for sensing and, processing an input signal and converting it to a set of control signals that are sent to the implantable pulse generator, wherein the set of control signals define spatiotemporal patterns of electrical stimuli that are applied through the spaced-apart electrode contacts; and
    means for automatically reducing the number of stimulation pulses applied to the more distally-located electrodes of the electrode array.

2. The cochlear implant system of claim 1 wherein the defined spatiotemporal patterns of electrical stimuli include fast stimulation rate pulse trains of narrow biphasic pulses that are applied to specific electrode contacts at specified times, and wherein said fast stimulation rate pulse trains are aimed at increasing temporal fine structure while also activating a stochastic resonance mode.

3. The cochlear implant system of claim 2 wherein the means for automatically reducing the number of stimulation pulses applied to the more distally-located electrodes comprise:
    means for identifying which of the narrow biphasic pulse trains are intended for delivery to the more distally-located electrodes of the electrode array, and
    means for removing a selected number of pulses from the biphasic pulse trains that are intended for delivery to the more-distally-located electrodes of the electrode array.

4. The cochlear implant system of claim 3 further including means for widening the pulse widths of the pulses remaining in the biphasic pulse trains.

5. The cochlear implant system of claim 3 further including means for decreasing the amplitude of the pulses remaining in the biphasic pulse trains.

6. The cochlear implant system of claim 3 wherein the means for automatically reducing the number of stimulation pulses applied to the more distally-located electrodes comprise:
    means for identifying which of the narrow biphasic pulse trains are intended for delivery to the more distally-located electrodes of the electrode array, and
    means for lowering the stimulation rate of the biphasic pulse trains intended for delivery to the more-distally-located electrodes of the electrode array.

7. The cochlear implant system of claim 6 further including means for widening the pulse widths of the pulses remaining in the biphasic pulse trains.

8. The cochlear implant system of claim 6 further including means for decreasing the amplitude of the pulses remaining in the biphasic pulse trains.

9. The cochlear implant system of claim 6 wherein the means for lowering the stimulation rate of the biphasic pulse trains intended for delivery to the more-distally-located electrodes of the electrode array comprises an algorithm that, when applied, reduces the stimulation rate as a function of the electrode contact through which the stimulus is to be applied.

10. The cochlear implant system of claim 9 wherein the algorithm comprises:

$$F_P(E_n) = 1 / [(M/2) + (1 - E_n)]$$

where
- $F_P$ is the stimulation rate that is applied as a function of the electrode number,
- $E_n$, expressed as a fraction of the form 1/p, where only 1 out of every p pulses is delivered to the electrode; and
- M is the number of electrodes.

11. The cochlear implant system of claim 10 wherein the number of electrodes, M, is sixteen, and wherein, if the stimulus electrode is E1, or $E_n=1$, then the cathode is E1, or the most distal electrode, and the algorithm reduces to:

$$F_P = 1/[8 + (1-1)] = 1/8;$$

whereby only one out of every 8 pulses that would have been applied to electrode E1 is applied to electrode E1 when the algorithm is used to implement the invention.

12. A method of operating a cochlear implant system comprising:
- implanting an electrode array having a multiplicity of spaced-apart electrode contacts at or near a distal end;
- electrically connecting an implantable pulse generator to the spaced-apart electrode contacts of the electrode array;
- sensing and processing an input signal and converting it to a set of control signals, wherein the set of control signals define spatiotemporal patterns of electrical stimuli that are to be applied through the spaced-apart electrode contacts;
- sending the set of control signals to the implantable pulse generator to cause the implantable pulse generator to generate stimulation pulses for application to the spaced-apart electrode contacts; and
- reducing the number of stimulation pulses applied to the more distally-located electrode contacts of the electrode array.

13. The method of operating a cochlear implant system of claim 12 wherein reducing the number of stimulation pulses applied to the more distally-located electrode contacts comprises applying the following algorithm:

$$F_P(E_n) = 1 / [(M/2) + (1 - E_n)]$$

where
- $F_P$ is the stimulation rate that is applied as a function of the electrode number,
- $E_n$, expressed as a fraction of the form 1/p, where only 1 out of every p pulses is delivered to the electrode; and
- M is the number of electrodes.

14. An implantable neural stimulation system comprising:
- an electrode array having a multiplicity of spaced-apart electrode contacts at or near a distal end;
- an implantable pulse generator electrically connected to the electrode contacts of the electrode array;
- processing means for sensing and processing an input signal and converting it to a set of control signals that are sent to the implantable pulse generator, wherein the set of control signals define spatiotemporal patterns of electrical stimuli that are applied through the spaced-apart electrode contacts; and
- means for automatically reducing the number of stimulation pulses applied to the more distally-located electrodes of the electrode array.

* * * * *